(12) United States Patent
Cygan

(10) Patent No.: US 8,524,832 B2
(45) Date of Patent: Sep. 3, 2013

(54) BIODEGRADABLE IMPACT-MODIFIED POLYMER COMPOSITIONS

(75) Inventor: Zuzanna Cygan, Wayne, PA (US)

(73) Assignee: Arkema Inc., King of Prussia, PA (US)

( * ) Notice: Subject to any disclaimer, the term of this patent is extended or adjusted under 35 U.S.C. 154(b) by 166 days.

(21) Appl. No.: 12/996,119

(22) PCT Filed: May 29, 2009

(86) PCT No.: PCT/US2009/045568
§ 371 (c)(1),
(2), (4) Date: Dec. 3, 2010

(87) PCT Pub. No.: WO2009/151977
PCT Pub. Date: Dec. 17, 2009

(65) Prior Publication Data
US 2011/0082224 A1    Apr. 7, 2011

Related U.S. Application Data

(60) Provisional application No. 61/061,323, filed on Jun. 13, 2008.

(51) Int. Cl.
*C08G 63/48* (2006.01)

(52) U.S. Cl.
USPC .......... 525/64; 525/69; 525/70; 525/71; 525/190; 528/354

(58) Field of Classification Search
USPC .......... 525/64, 69, 70, 71, 190; 528/354
See application file for complete search history.

(56) References Cited

U.S. PATENT DOCUMENTS

| | | | |
|---|---|---|---|
| 7,368,503 B2 | 5/2008 | Hale | |
| 7,589,151 B2 * | 9/2009 | Aoki et al. | 525/64 |
| 8,183,321 B2 * | 5/2012 | Babcock et al. | 525/64 |
| 2007/0264481 A1 | 11/2007 | DeSimone et al. | |
| 2008/0112886 A1 | 5/2008 | Mitragotri et al. | |
| 2008/0181958 A1 | 7/2008 | Rothrock et al. | |
| 2009/0020789 A1 | 1/2009 | Shiraki et al. | |
| 2009/0028910 A1 | 1/2009 | DeSimone et al. | |
| 2009/0061152 A1 | 3/2009 | DeSimone et al. | |
| 2010/0028994 A1 | 2/2010 | DeSimone et al. | |
| 2010/0144971 A1 | 6/2010 | Babcock et al. | |
| 2010/0147365 A1 | 6/2010 | DeSimone et al. | |

FOREIGN PATENT DOCUMENTS

| | | | |
|---|---|---|---|
| WO | WO 2008/051443 | * | 5/2008 |
| WO | WO 2008/063988 | | 5/2008 |

* cited by examiner

*Primary Examiner* — John Cooney
(74) *Attorney, Agent, or Firm* — Lynn B. Morreale

(57) ABSTRACT

The invention relates to a impact-modified bio-degradable polymer composition having large particle size impact modifiers dispersed in a continuous biodegradable polymer phase. The impact modifiers have a core-shell morphology and have average sizes of greater than 250 nm. The impact-modified composition has good impact properties and low haze. The biodegradable polymer is preferably a polylactide or polyhydroxy butyrate. The composition comprises 30-99.9 weight percent of degradable polymer and 0.1 to 15 weight percent of one or more impact modifiers.

14 Claims, No Drawings

BIODEGRADABLE IMPACT-MODIFIED POLYMER COMPOSITIONS

FIELD OF THE INVENTION

The invention relates to a impact-modified bio-degradable polymer composition having large particle size impact modifiers dispersed in a continuous biodegradable polymer phase. The impact modifiers have of the core-shell morphology and have average sizes of greater than 250 nm. The impact-modified composition has good impact properties and low haze.

BACKGROUND OF THE INVENTION

The growing global concern over persistent plastic waste has generated much interest in biodegradable polymers for everyday use. Biodegradable polymers based on polylactic acid (PLA) are one of the most attractive candidates as they can be readily produced from renewal agricultural sources such as corn. Recent developments in the manufacturing of the polymer economically from agricultural sources have accelerated the polymers emergence into the biodegradable plastic commodity market.

Linear acrylic copolymers have been disclosed for use as process aids in a blend with a biopolymer, such as polylactide. (US Application 2007-0179218). The disclosed linear acrylic copolymers do not provide satisfactory impact properties. Additives such as impact modifiers could be used in the polylactide composition.

One problem with many biodegradable polymers, such as polylactide, is the very brittle nature of the pure polymer. This property results in very low impact properties of finished articles, much lower than what is desirable for adequate product performance. Impact modifiers, such as methylmethacrylate-butadiene-styrene (MBS) and acrylic core-shell or block copolymers, are known to improve the impact properties of PVC and polycarbonate blends.

Block copolymers and core-shell polymers have been described for use in biodegradable polymers in PCT/US07/84502. This application is silent of particle size.

WO 2008/051443 describes clear impact modified polylactide resins. The resins are modified with bimodal core-shell impact modifiers, and the number average particle size of all particles and agglomerates in less than 210 nanometers.

Surprisingly it has been found that core-shell impact modifiers having a number average particle size of greater than 250 can be used in a biodegradable plastic, and still achieve excellent impact modification and low haze.

SUMMARY OF THE INVENTION

The invention relates to a biodegradable polymer composition comprising:
  a) 30 to 99.9 weight percent of one or more biodegradable polymers;
  b) 0-69.9 weight percent of one or more biopolymer; and
  c) 0.1 to 15 weight percent of one or more core-shell impact modifiers,
wherein said impact modifiers have a number average particle size of greater than 250 nm.
The biodegradable polymer composition may be clear or translucent, and preferably has a haze of less than 15.

DETAILED DESCRIPTION OF THE INVENTION

The biodegradable polymer of the invention can be a single biodegradable polymer, or a mixture of biodegradable polymers. Some examples of biodegradable polymers useful in the invention include, but are not limited to, polylactide and polyhydroxy butyrate. The biodegradable composition comprises 30 to 99.9 weight percent of the one or more biodegradable polymers.

The preferred polylactide and polyhydroxy butyrate can be a normal or low molecular weight.

In addition to the biodegradable polymer(s), other biopolymers, such as, but not limited to starch, cellulose, and polysaccharides may also be present. Additional biopolymers, such as but not limited to polycaprolactam, polyamide 11 and aliphatic or aromatic polyesters may also be present. The other bio-polymers may be present in the composition at from 0-69.9 weight percent.

One or more impact modifiers is used at from 0.1 to 15 weight percent of the composition.

The impact modifier is a core/shell impact modifier. The core-shell (multi-layer) impact modifiers could have a soft (rubber or elastomer) core and a hard shell, a hard core covered with a soft elastomer-layer, and a hard shell, of other core-shell morphology known in the art. The rubber layers are composed of low glass transition (Tg) polymers, including, but not limited to, butyl acrylate (BA), ethylhexyl acrylate (EHA), butadiene (BD), butylacrylate/styrene, and many other combinations. In a preferred, the core is an all-acrylic homopolymer or co-polymer. It has been found that acrylic cores lead to a biodegradable polymer composition having lower haze than with the diene core polymers.

The preferred glass transition temperature (Tg) of the elastomeric layer should be below 25° C. The elastomeric or rubber layer is normally crosslinked by a multifunctional monomer for improved energy absorption. Crosslinking monomers suitable for use as the crosslinker in the core/shell impact modifier are well known to those skilled in the art, and are generally monomers copolymerizable with the monounsaturated monomer present, and having ethylenically multifunctional groups that have approximately equal reactivity. Examples include, but are not limited to, divinylbenzene, glycol of di- and trimethacrylates and acrylates, triol triacrylates, methacrylates, and allyl methacrylates, etc. A grafting monomer is also used to enhance the interlayer grafting of impact modifiers and the matrix/modifier particle grafting. The grafting monomers can be any polyfunctional crosslinking monomers.

For soft core multi-layered impact modifies, the core ranges from 30 to 95 percent by weight of the impact modifier, and outer shells range from 15-70 weight percent. The crosslinker in the elastomeric layer ranges from 0 to 5.0%. The synthesis of core-shell impact modifiers is well known in the art, and there are many references, for example U.S. Pat. No. 3,793,402, U.S. Pat. No. 3,808,180, U.S. Pat. No. 3,971,835, and U.S. Pat. No. 3,671,610, incorporated herein by reference. The refractive index of the modifier particles, and/or matrix polymer, can be matched against each other by using copolymerizable monomers with different refractive indices. Preferred monomers include, but are not limited to, styrene, alpha methylstyrene, and vinylidene fluoride monomers having unsaturated ethylenic group.

Other non-core/shell impact modifiers are also possible for use in this invention, where super transparency and clarity may not be required. For example butadiene rubber can be incorporated into an acrylic matrix to achieve high ballistic resistance property.

In a preferred embodiment, the core-shell polymer is 80-90% of an acrylic core, and a shell comprised of 75-100 weight % methyl methacrylate, 0-20 weight percent butyl acrylate and 0-25 weight percent ethyl acrylate. The acrylic core is preferably selected from a butyl acrylate homopolymer, and ethylhexyl acrylate homopolymer, or a copolymer of butyl acrylate and ethylhexyl acrylate at any monomer ratio.

In one embodiment, the acrylic copolymer impact modifier is an acrylate based copolymer with a core-shell polymer having a rubbery core, such as 1,3-dienes (also copolymers with vinyl aromatics) or alkyl acrylates with alkyl group containing 4 or more carbons and the shell is grafted onto the core and is comprised of monomers such as vinyl aromatics (e.g., styrene), alkyl methacrylates (alkyl group having 1-4 carbons), alkyl acrylates (alkyl group having 1-4 carbons), and acrylonitrile.

A preferred acrylic type core/shell polymer is one having a 70-90% core of 0-100 weight % butylacrylate, 0-100% 2-ethylhexyl acrylate and 0-35% butadiene, and a shell comprised of 75-100 weight % methyl methacrylate, 0-20 weight percent butyl acrylate and 0-25 weight percent ethyl acrylate.

The core-shell impact modifier of the invention has a number average particle size of over 250 nm, preferably from 250 to 400 nm, and most preferably from 280 to 330 nm. The core-shell impact modifier can be a blend of two or more sizes or chemical compositions, however the number average particle size of all the impact modifier particles is greater than 250 nm.

The bio degradable polymer composition of the invention contains 30-99.9 weight percent of the biodegradable polymer, 0-69.9 weight percent of other biopolymers and from 0.1-15 weight percent of the acrylic copolymer(s). The ingredients may be admixed prior to processing, or may be combined during one or more processing steps, such as a melt-blending operation. This can be done, for instance by single-screw extrusion, twin-screw extrusion, Buss kneader, two-roll mill, impeller mixing. Any admixing operation resulting in a homogeneous distribution of acrylic-methacrylic copolymer in the biodegradable polymer is acceptable. Formation of the blend is not limited to a single-step formation. Masterbatch formation of 15-99% acrylic-methacrylic copolymer in 1-85% carrier polymer followed by subsequent addition to the biodegradable polymer to derive a final blend is also anticipated. The carrier polymer may be, but is not limited to, polylactide, acrylic-methacrylic copolymers, and methacrylic homopolymers.

In addition to the biodegradable polymer, biopolymer and impact modifier adding up to 100 percent, the composition of the invention may additionally contain a variety of additives, including but not limited to, heat stabilizers, internal and external lubricants, other impact modifiers, process aids, melt strength additives, fillers, and pigments.

The composition of the invention was found to have greatly improved the impact properties over the polylactide alone. The core-shell polymer impact modifiers provide excellent impact modification, while still providing a low haze.

The impact-modified biodegradable polymer composition can range from almost clear or translucent, to opaque, depending on the composition and level of impact modification. In one embodiment, the impact-modified biodegradable polymer has a haze level of below 15 percent, preferably below 12 percent when measured by ASTM 1003-00.

The composition of the invention can be processed using any known method, including but not limited to injection molding, extrusion, calendaring, blow molding, foaming and thermoforming. Useful articles that can be made using the biodegradable composition, include but are not limited to packaging materials, films and bottles. One in the art can imagine a variety of other useful articles and processes for forming those articles, based on the disclosure and examples herein.

EXAMPLES

Example 1

Blends of 95 and 93.5% polylactide containing 5 and 7.5% by weight of acrylic-methacrylic copolymer impact modifier was formed by melt extrusion using a twin-screw extruder. The processing temperature and melt temperature during extrusion were maintained above the melting temperature of polylactide (>152° C.) to ensure a homogeneous melt. The extrudate was cast into a sheet (17-22 mil) using a 3 roll stack and puller. Haze measurements were performed on the sheet using a Colormeter and dart drop impact measurements were performed with a Gardner Impact tester with a 2 lb hemispherical impactor head. The data observed is shown in Table 1 below:

TABLE 1

|  | particle size | mean failure energy [ft lb] | haze |
|---|---|---|---|
| 5% modifier |  |  |  |
| A | 280 | 7.0 | 5.0 |
| B | 330 | 6.1 | 7.3 |
| C | 450 | 7.6 | 24.3 |
| 7.5% modifier |  |  |  |
| A | 280 | 10.5 | 9.9 |
| B | 330 | 10.3 | 9.2 |
| C | 450 | 15.4 | 48.6 |

What is claimed is:

1. A biodegradable polymer composition comprising:
   a) 30 to 99.9 weight percent of one or more biodegradable polymers;
   b) 0 to 69.9 weight percent of one or more biopolymers; and
   c) 0.1 to 15 weight percent of one or more core-shell impact modifiers,
   wherein said impact modifiers have a number average particle size of greater than 250 nm, and wherein said composition has a haze of less than 15 percent as measured by ASTM 1003-00.

2. A biodegradable polymer composition of claim 1, wherein said biodegradable polymer is polylactide, polyhydroxy butyrate, or a mixture thereof.

3. The biodegradable polymer composition of claim 1, wherein said impact modifier has a number average particle size of from greater than 250 nm to 400 nm.

4. The biodegradable polymer composition of claim 1, wherein said impact modifier has a number average particle size of from 280 to 330 nm.

5. The biodegradable polymer composition of claim 2, wherein said polylactide has a weight average molecular weight of from 10,000-3,000,000 g/mol.

6. The biodegradable polymer composition of claim 1 wherein the core-shell impact modifier are a blend of two or more copolymers.

7. The biodegradable polymer composition of claim 1, wherein said biopolymer comprises one or more polymers selected from the group consisting of starch, cellulose, polysaccharides, aliphatic or aromatic polyesters, and polycaprolactone.

8. The biodegradable polymer composition of claim 1, wherein said core-shell impact modifier is an all-acrylic core/shell polymer.

9. The biodegradable polymer composition of claim 1, wherein the core of said core-shell impact modifier comprises one or more monomer units selected from the group consisting of butyl acrylate, and ethylhexylacrylate.

10. The biodegradable polymer composition of claim 1, wherein the core of said core-shell impact modifier is polybutyl acrylate.

11. A formed article comprising the biodegradable polymer composition of claim 1.

12. The biodegradable polymer composition of claim 1, wherein the biopolymer comprises one or more of starch, cellulose, and polycaprolactone.

13. An article formed according to claim 11, wherein the article is packaging material, a film, or a bottle.

14. The biodegradable polymer composition according to claim 1, wherein the shell of the core/shell impact modifier comprises 75.400 weight % methyl methacrylate, 0-20 weight percent butyl acrylate and 0-25 weight percent ethyl acrylate.

* * * * *